US008021146B2

(12) United States Patent
Cinader, Jr. et al.

(10) Patent No.: US 8,021,146 B2
(45) Date of Patent: Sep. 20, 2011

(54) APPARATUS AND METHODS FOR CONTROLLING MOISTURE DURING ORTHODONTIC INDIRECT BONDING PROCEDURES

(75) Inventors: David K. Cinader, Jr., Yorba Linda, CA (US); Raymond P. Johnston, Lake Elmo, MN (US); David S. Arney, St. Paul, MN (US); Oliver L. Puttler, La Crescenta, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 11/422,613

(22) Filed: Jun. 7, 2006

(65) Prior Publication Data
US 2007/0287120 A1 Dec. 13, 2007

(51) Int. Cl.
*A61C 3/00* (2006.01)
(52) U.S. Cl. .......................................................... 433/3
(58) Field of Classification Search ................ 433/2, 3, 433/8, 9, 24, 6, 80, 215
See application file for complete search history.

(56) References Cited

U.S. PATENT DOCUMENTS

| 4,360,341 A | 11/1982 | Dellinger |
| 4,501,554 A | 2/1985 | Hickham |
| 4,551,096 A | 11/1985 | Dellinger |
| 4,657,508 A | 4/1987 | Dellinger |
| 5,059,118 A | 10/1991 | Breads et al. |
| 5,971,754 A | 10/1999 | Sondhi et al. |
| 5,980,249 A * | 11/1999 | Fontenot ........................ 433/80 |
| 6,123,544 A | 9/2000 | Cleary |
| 6,126,443 A | 10/2000 | Burgio |
| 6,142,780 A | 11/2000 | Burgio |
| 6,299,440 B1 | 10/2001 | Phan et al. |
| 6,497,575 B2 * | 12/2002 | Zavitsanos et al. ........... 433/215 |
| 6,607,382 B1 | 8/2003 | Kuo et al. |
| 7,020,963 B2 | 4/2006 | Cleary et al. |
| 7,364,428 B2 | 4/2008 | Cinader, Jr. et al. |
| 2002/0081555 A1* | 6/2002 | Wiesel ........................ 433/215 |
| 2004/0209218 A1 | 10/2004 | Chishti et al. |
| 2004/0219471 A1 | 11/2004 | Cleary et al. |
| 2004/0219473 A1 | 11/2004 | Cleary et al. |
| 2004/0253562 A1 | 12/2004 | Knopp |
| 2005/0074716 A1 | 4/2005 | Cleary et al. |
| 2005/0133384 A1 | 6/2005 | Cinader et al. |
| 2005/0136370 A1 | 6/2005 | Brennan et al. |
| 2005/0244790 A1 | 11/2005 | Kuperman |
| 2005/0277084 A1 | 12/2005 | Cinader et al. |
| 2006/0029908 A1* | 2/2006 | Allred et al. .................. 433/215 |
| 2006/0223021 A1 | 10/2006 | Cinader, Jr. et al. |
| 2006/0223031 A1 | 10/2006 | Cinader, Jr. et al. |
| 2006/0257821 A1 | 11/2006 | Cinader, Jr. et al. |

FOREIGN PATENT DOCUMENTS
KR 1020010038279 5/2001
* cited by examiner

*Primary Examiner* — Sunil K Singh
(74) *Attorney, Agent, or Firm* — Kevin W. Weber

(57) ABSTRACT

An indirect bonding tray for orthodontic bonding procedures has moisture control structure that is located next to the patient's teeth when the tray is placed over the patient's dental arch. The moisture control structure tends to draw moisture away from the adhesive used to bond the appliances to the teeth. As a consequence, the probability that the resulting bond between the appliances and the teeth is adversely affected by the presence of moisture, blood or other fluids in the patient's mouth is decreased.

15 Claims, 4 Drawing Sheets

APPARATUS AND METHODS FOR CONTROLLING MOISTURE DURING ORTHODONTIC INDIRECT BONDING PROCEDURES

BACKGROUND OF THE INVENTION

1. Field of the Invention

This invention broadly relates to orthodontic indirect bonding procedures for affixing orthodontic appliances to the patient's teeth. More particularly, the present invention is directed towards apparatus and methods for controlling moisture such as saliva during indirect bonding procedures.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In general, orthodontic appliances that are adapted to be adhesively bonded to the patient's teeth are placed and connected to the teeth by either one of two procedures: A direct bonding procedure, or an indirect bonding procedure. In the direct bonding procedure, the appliance is grasped with a pair of tweezers or other hand instrument and placed by the practitioner on the surface of the tooth in its desired location, using a quantity of adhesive to fix the appliance to the tooth. In the indirect bonding procedure, a transfer tray is constructed with wall sections having a shape that matches the configuration of at least part of the patient's dental arch, and a set of appliances such as orthodontic brackets are releasably connected to the tray at certain, predetermined locations. After an adhesive is applied to the base of each appliance, the tray is placed over the patient's teeth and remains in place until such time as the adhesive has hardened. Next, the tray is detached from the teeth as well as from the appliances, with the result that all of the appliances previously connected to the tray are now bonded to the respective teeth at their intended, predetermined locations.

Indirect bonding techniques offer a number of advantages over direct bonding techniques. For example, it is possible with indirect bonding techniques to bond a plurality of appliances to a patient's dental arch simultaneously, thereby avoiding the need to bond each appliance in individual fashion. In addition, the transfer tray helps to locate the appliances in their proper, intended positions such that adjustment of each appliance on the surface of the tooth before bonding is avoided. The increased accuracy of the appliances that is often afforded by indirect bonding procedures helps ensure that the patient's teeth are moved to their proper, intended positions at the conclusion of treatment.

The control of moisture during a bonding procedure is often deemed important, since the presence of moisture can adversely affect the resultant bond strength between the appliance and the tooth. If, for example, the appliance inadvertently detaches from the tooth during the course of treatment, the patient must often return to the practitioner's office for rebonding of the appliance or replacement of the appliance before full treatment can resume. Obviously, unintentional debonding of orthodontic appliances is a nuisance to both the practitioner and to the patient that is best avoided if at all possible.

In the past, a variety of methods were used to reduce the presence of moisture in the patient's oral cavity during orthodontic bonding procedures. For example, some practitioners use absorbent articles such as cotton rolls to absorb saliva and/or blood along with cheek retractors to help keep the mouth tissue in an open, stationary position. Other practitioners use suction devices such as Nola brand dry field cheek retractors that have suction tubing for drawing fluids out of the oral cavity. Other practitioners have proposed the use of an anti-sialagogue, a drug that can be used to dry the salivary glands during a bonding procedure.

The control of moisture during an indirect bonding procedure is often considered more challenging than controlling moisture during a direct bonding procedure. For one thing, in an indirect bonding procedure, it is important to simultaneously keep multiple bond sites dry. In addition, many indirect bonding trays have interior wall sections that closely fit the patient's teeth, and consequently tend to spread moisture over relatively large portions of the tooth surface as the tray is placed onto the dental arch.

SUMMARY OF THE INVENTION

The present invention relates to improved apparatus and methods for controlling moisture during orthodontic indirect bonding procedures. In particular, the present invention concerns an indirect bonding tray having structure attached to the tray for reducing moisture on the patient's tooth surfaces. As a result, the probability of a compromised adhesive bond and subsequent inadvertent detachment of the appliances during the course of treatment due to bond failure is reduced.

In more detail, the present invention in one aspect relates to apparatus for indirect bonding of orthodontic appliances. The apparatus includes a tray having a channel for receiving a patient's dental arch, and the channel includes an outer edge. A number of orthodontic appliances are detachably connected to the tray, and the appliances are located along a path in the channel. The apparatus also includes an elongated moisture control structure extending between the path of the appliances and the outer edge for reducing moisture in the channel in an area between the path and the outer edge.

Another aspect of the present invention is also directed toward an apparatus for indirect bonding of orthodontic appliances. In this aspect, the apparatus includes a tray having a channel for receiving a patient's dental arch, and a number of orthodontic appliances are detachably connected to the tray and located in the channel. A manifold is connected to the tray and includes an inlet spaced from the appliances. A source of potential is coupled to the manifold for drawing moisture through the inlet.

Another aspect of the present invention relates to a method for controlling moisture during orthodontic indirect bonding procedures. The method comprises:

detachably connecting a number of orthodontic appliances to a channel of an indirect bonding tray;

coupling moisture control structure to the tray; and placing the tray over the patient's dental arch such that the moisture control structure is located next to the patient's teeth in an area between the appliances and the patient's gingiva.

These and other aspects of the invention are described in more detail in the paragraphs that follow and are illustrated in the accompanying drawings.

BRIEF DESCRIPTIONS OF THE DRAWINGS

DEFINITIONS

Figure 1:
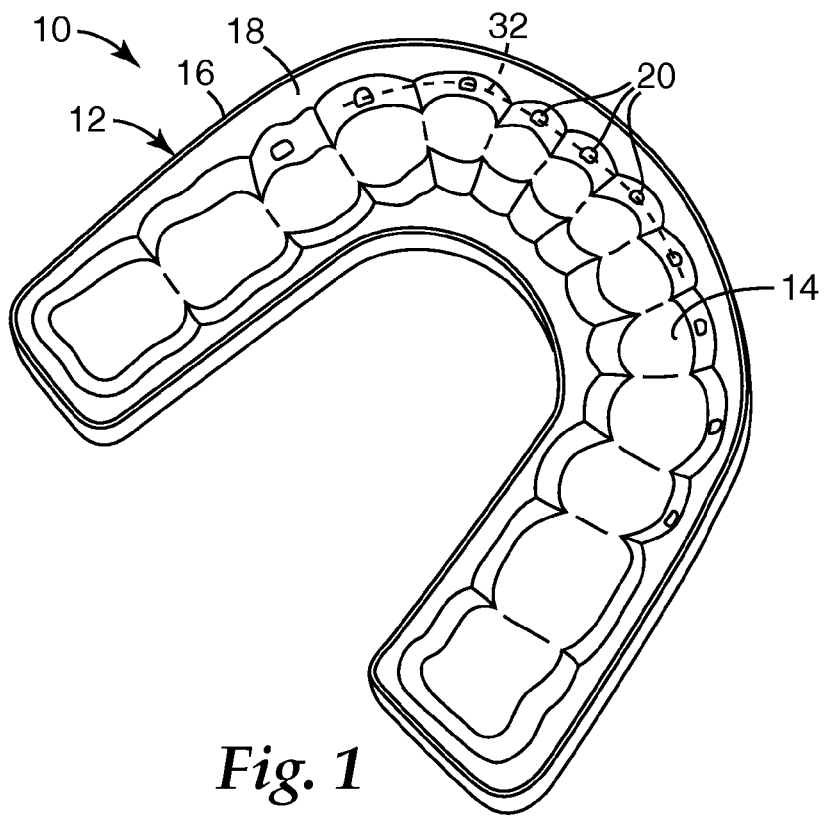
FIG. 1 is a perspective view of an apparatus for indirect bonding of orthodontic appliances constructed in accordance with one embodiment of the invention.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

DETAILED DESCRIPTION OF THE PREFERRED EMBODIMENTS

An apparatus for indirect bonding of orthodontic appliances according to one embodiment of the invention is illustrated in FIGS. 1-4 and is broadly designated by the numeral 10. The apparatus 10 includes a tray 12 having a channel 14 for receiving a patient's dental arch. In the exemplary tray 12 shown in the drawings, the channel 14 is adapted to receive a patient's lower dental arch, although it should be understood in this regard that as an alternative the tray 12 may be constructed to receive the patient's upper dental arch.

The tray 12 may be constructed according to any one of a variety of known techniques. In the example shown in FIGS. 1-4, the tray 12 includes an outer shell 16 that is relatively stiff and an inner section of matrix material 18 that is relatively flexible. A suitable material for the shell 16 is a sheet of polycarbonate such as Makrolon brand material from Bayer or Lexan brand polycarbonate from GE having a thickness of 0.06 in. (1.5 mm). Other materials, such as polyethyleneterephthalate ("PET"), polyethyleneterephthalate glycol ("PETG") may also be used.

Preferably, the matrix material 18 has a relatively low viscosity before hardening so that intimate contact between the matrix material 18 and orthodontic appliances received in the channel 14 is assured. In this manner, the matrix material 18 is able to substantially penetrate in various recesses, cavities and other structural features of each appliance so that a secure connection between the appliance and the matrix material 18 can be established. An example of a suitable matrix material having a relatively low viscosity before curing is a silicone material such as "RTV615" silicone material from General Electric.

The matrix material 18 preferably has a viscosity before curing that is less than about 60,000 cp. More preferably, the matrix material 18 has a viscosity before curing that is less than about 25,000 cp. Most preferably, the matrix material has a viscosity that is less than about 8,000 cp. Once hardened, the matrix material 18 has a Shore A hardness that is in the range of about 10 to about 80, more preferably in the range of about 30 to about 60 and most preferably in the range of about 40 to about 50.

Alternatively, the matrix material 18 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. Another suitable matrix material is Affinity Crystal brand silicone impression material from Clinician's Choice Dental Products, Inc. If a light-curable adhesive is to be subsequently used for bonding the appliances to the patient's teeth, the matrix material 18 is preferably optically clear and transmits actinic radiation without substantial absorption once hardened.

Preferably, the inner surface of the matrix material 18 that faces the channel 14 has contours that precisely match the contours of the individual teeth of the patient, as well as an overall configuration that matches the orientation of each tooth relative to other teeth in the same dental arch when the teeth are in their initial maloccluded condition at the beginning of treatment. As a result, when the tray 12 is placed over the patient's dental arch, the channel 14 of the tray 12 provides a mating fit with the patient's teeth such that little, if any, tolerance or "slop" is present and relative movement between the tray and the dental arch is substantially hindered.

Figure 2:
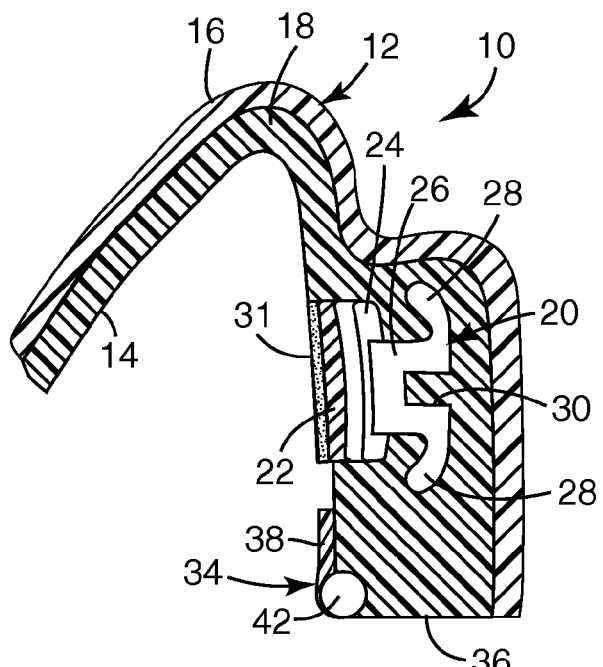
FIG. 2 is an enlarged side cross-sectional view of the apparatus depicted in FIG. 1.
Figure 4:
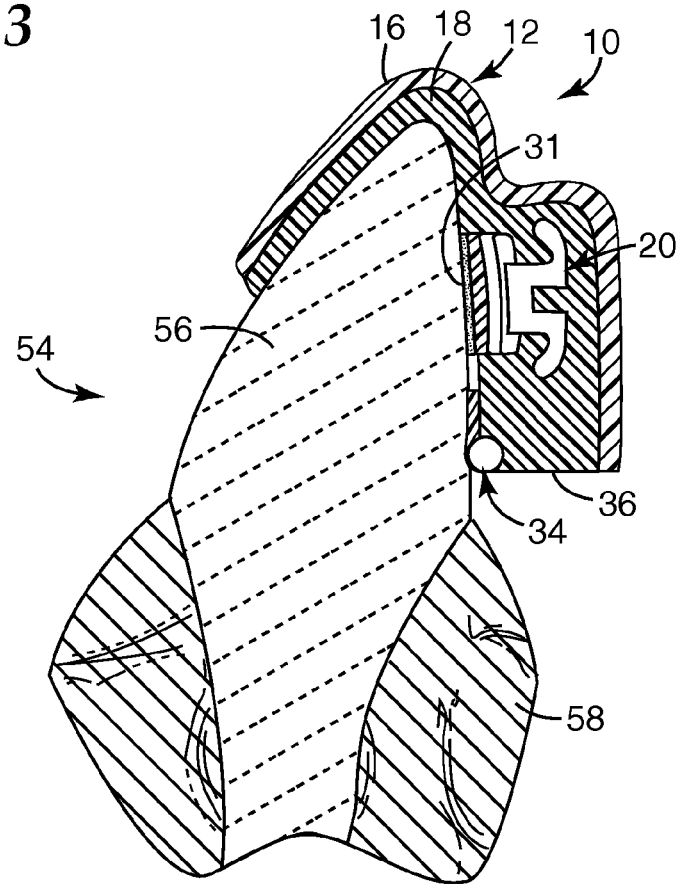
FIG. 4 is a side cross-sectional view in somewhat smaller scale illustrating the apparatus of FIGS. 1-3 as it appears when placed over the teeth of a dental arch.

The apparatus 10 also includes a number of orthodontic appliances 20 that are detachably connected to the tray 12. In FIGS. 2 and 4, the exemplary orthodontic appliance 20 is an orthodontic bracket, although other appliances are also possible. Examples of other suitable appliances include buccal tubes, buttons, formed "bumps" made, e.g., of composite material, or any other metal or non-metal "handle" or other structure connected to the teeth that provides an attachment point for a force member such as a wire, aligner tray, polymeric strip, elastomeric band or chain, or any combination of the foregoing. If desired, appliances may be omitted for some of the teeth in the dental arch such as molar teeth or teeth that have only partially erupted.

The exemplary appliance 20 as shown in FIGS. 2 and 4 includes a base 22 that is connected to a base flange 24. The appliance 20 also has a body 26 that extends outwardly from the base flange 24. A pair of tiewings 28 is connected to the body 26, and an archwire slot 30 extends through a space between the tiewings 28.

The base flange 24, the body 26 and the tiewings 28 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina) and plastic materials (such as fiber-reinforced polycarbonate). Optionally, the base flange 24, the body 26 and the tiewings 28 are integrally made as a unitary component.

The base 22 of the appliance 20 is preferably made of a material different than the material comprising the base flange 24, and has a configuration that matches the configuration of a portion of a patient's tooth structure. More particularly, the base 22 has a concave contour that is a replica of the convex contour of the portion of the patient's tooth that represents the ultimate desired location of the appliance 20 on the tooth. Optionally, the concave contour of the base 22 is a compound concave contour (i.e., curved in directions along two mutually perpendicular reference planes).

The bonding adhesive 31 may be any orthodontic adhesive suitable for use as an indirect bonding adhesive. Optionally, the adhesive 31 is a two-component adhesive, wherein the first component is Transbond brand XT primer and the second component is Transbond brand Plus self-etching primer, both from 3M Unitek. The first component of such two component adhesive is applied to the base 22 and the second component is applied to the area of each patient's tooth that is to receive the appliance 20.

Another option is to use a preliminary teeth etching step (such as by exposing the teeth to 37% phosphoric acid or equivalent), followed by applying a suitable chemical curing adhesive. Examples of suitable chemical curing adhesives include Sondhi brand Rapid-Set indirect bonding adhesive and Unite brand adhesive, both from 3M Unitek Corporation. The Sondhi brand adhesive includes two lightly filled resin components that are mixed independently from each other and applied to the teeth and to the appliances respectively. The Unite brand adhesive, on the other hand, includes a mixed resin component and a mixed paste component; the resin component is first applied to both the teeth and the appliances, and then the paste component is applied to the appliances to form a so-called "sandwich" configuration. Another suitable two-component adhesive is Concise brand adhesive, also from 3M Unitek Corporation. The Concise brand adhesive includes a mixed paste component along with a mixed resin component that are placed on the appliances and teeth respectively. Alternatively, a resin-modified glass ionomer cement may be applied. Glass ionomer cements provide an additional advantage in that a separate tooth etching step is unnecessary.

Optionally, the bases 22 may be precoated with an orthodontic adhesive by the manufacturer as described in Published U.S. Patent Application No. 2005/0074716-A1. Optionally, the precoated adhesive may have multiple layers and/or be patterned, as described in Published U.S. Patent Application No. 2005/0136370. As an additional option, the adhesive 31 may vary from one appliance 20 to the other as described in Published U.S. Patent Application No. 2005/0133384-A1.

The appliances 20 extend along a path 32 that is represented by the dashed line in FIG. 1. The path 32 may or may not be a curved line that extends in a reference plane parallel to the patient's occlusal plane depending on the practitioner's preferred treatment technique. For example, if the practitioner employs the "straight wire" technique, the path 32 of the appliances 20 may lie in a common place at the conclusion of treatment but typically will not lie in a common plane at the beginning of treatment.

Figure 2A:
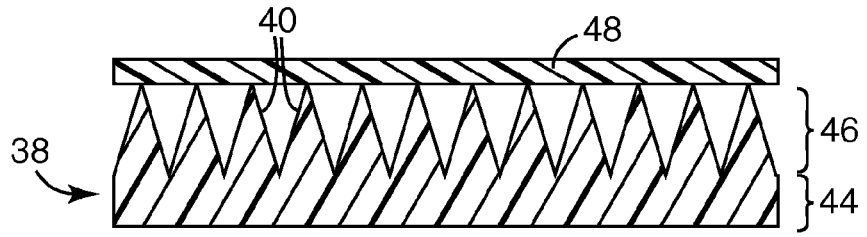
FIG. 2A is an enlarged side cross-sectional view of part of a moisture control structure of the apparatus shown in FIGS. 1-2.

The apparatus 10 also includes an elongated moisture control structure 34 (not shown in FIG. 1) that extends between the path 32 of the appliances 20 and an outer edge 36 of the tray 12. In this embodiment, the moisture control structure 34 includes a film 38 having a plurality of flow channels or passages 40 (FIG. 2A). The passages 40 are in communication with a manifold 42 located next to the outer edge 36 of the tray 12.

An enlarged cross-sectional view of the film 38 alone is shown in FIG. 2A. As illustrated, the film 38 includes a body layer 44 and a structured surface 46 connected to the body layer 44. The structured surface 46 presents a series of lined V-shaped side walls, which define the passages 40. Preferably, the passages 40 are arranged in a parallel array, although other configurations are also possible.

A cap layer 48 extends over and is coupled to the structured surface 46. In this embodiment, the cap layer 48 is a nonporous flexible film material that is bonded or otherwise affixed to the structured surface 46. The passages 40 have open ends that represent a plurality of inlets that are located adjacent the enamel surface of the patient's tooth and next to the bases 22 of the appliances 20.

Preferably, the inlets extend continuously along a substantial majority of the length of the channel 14 of the tray 12, and more preferably along the entire length of the channel 14. Consequently, oral fluids such as saliva and blood will be drawn through the inlets presented by the passages 40 and into the manifold 42 when a potential source such as a vacuum is applied to the manifold 42.

The manifold 42 includes a plenum that is in fluid communication with open ends of the passages 40 remote from the appliances 20. As one example, the manifold 42 may comprise plastic tubing with a plurality of openings in communication with ends of the passages 40. In this embodiment, the manifold 42 extends substantially along the entire length of the outer edge 36 of the tray 12 and is substantially equal in length to the length of the film 38.

Figure 3:
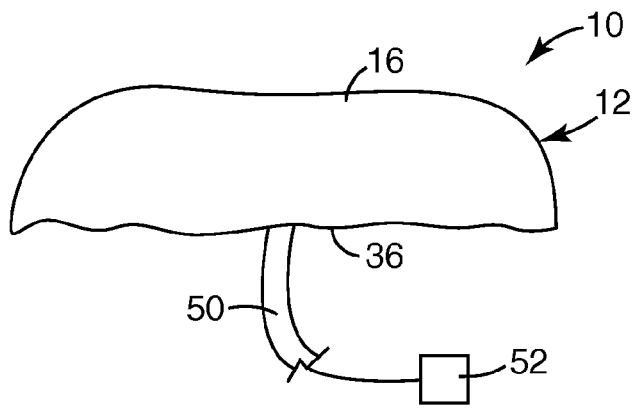
FIG. 3 is a front elevational view of the apparatus shown in FIGS. 1 and 2 along with a schematic depiction of a source of vacuum.

As illustrated in FIG. 3, an outlet tubing 50 is connected to the manifold 42 in an area near the center of the manifold 42, which corresponds to a region near the middle of the patient's dental arch. The tubing 50 has an interior passageway that is in communication with the plenum of the manifold 42. The passageway of the tubing 50 is also connected to a source of potential such as a source of vacuum 52 that is schematically depicted in FIG. 3.

"Vacuum", as used herein, shall mean any air pressure that is less than atmospheric pressure, and does not mean an absolute vacuum. Other potential sources may be used in the present invention instead of or in combination with the source of vacuum 52. Essentially any manner of causing or encouraging liquid flow through the passages 40 is contemplated in this invention. Examples of potential sources include vacuum pumps, vacuum aspirators, pressure pumps, hydrostatic heads and gravity, and/or any other fluid drive system utilizing the creation of a potential difference that urges the fluid to flow to some extent.

Examples of suitable films 38 and methods of making such films are described in U.S. Pat. No. 6,290,685 (Insley et al.), U.S. Pat. No. 6,531,206 (Johnston et al.), U.S. Pat. No. 6,080,243 (Insley et al.) and U.S. Pat. No. 5,728,446 (Johnston et al.).

As an alternative construction, the cap layer 48 is replaced by a liquid sorbing layer that is permeable to oral fluids. In this alternative, each passage effectively has an open side that represents an elongated inlet for receiving fluids. As such, a larger area of the tooth surface between the path 32 of the appliances 20 and the outer edge 36 is covered by inlets. Suitable materials for the liquid sorbing layer include nonwoven webs, particularly those containing meltblown microfibers and microfiber microwebs. An example of a suitable web material is disclosed in U.S. Pat. No. 4,813,948 to Insley. Preferably, the liquid sorbing layer also can function as a collector or reservoir for liquid before it is drawn into the passages 40.

Suitable methods for making the tray 12 are described in U.S. Pat. No. 7,020,963, published U.S. Patent Application No. 20040219473 and pending U.S. patent application Ser. No. 11/098317, entitled "METHOD OF MAKING INDIRECT BONDING APPARATUS FOR ORTHODONTIC THERAPY". Preferably, the tray 12 also includes occlusal stops such as described in Pending U.S. patent application Ser. No. 11/098716, entitled "ORTHODONTIC INDIRECT BONDING APPARATUS WITH OCCLUSAL POSITIONING STOP MEMBERS".

As one option to make the apparatus 10, the shell 16 may be constructed as described in the preceding patent applications by initially placing spacer material over a dental model of the patient's arch. After the shell 16 is formed, the spacer material is removed from the dental arch model, and the film 38 and manifold 42 are then positioned as desired the arch model using a temporary, releasable adhesive. Next, the outer shell 16 is placed over the dental model, the film 38 and the manifold 42. Subsequently, uncured matrix material 18 is added to the space between the shell 16 and the model and allowed to cure.

FIG. 4 is an illustration showing an exemplary use of the apparatus during an orthodontic bonding procedure. As shown, the tray 12 is placed over the dental arch 54, causing the base 22 of the appliance 20 to contact the enamel surface of the patient's tooth 56. When the tray 12 is positioned in this manner, the inlets of the film 38 are located next to the patient's tooth surfaces and between the base 22 of the appliances 20 and the patient's gingiva 58 in order to remove moisture in an area near the adhesive 31 associated with each appliance 20.

Preferably, the source of vacuum 52 is activated before or simultaneously with placement of the apparatus 10 over the dental arch 54. As a consequence, moisture is drawn away from the adhesive 31 before the adhesive 31 has cured and during the time period that the adhesive 31 is curing.

After the adhesive 31 has cured, the apparatus 10 is removed from the patient's dental arch 54. Preferably, the shell 16 is first separated from the matrix material 18, which remains in place over the dental arch 54 along with the appliances 20. Next, the matrix material 18 is detached from the appliances 20. A hand instrument such as a scaler may be used to help hold each appliance 20 against the surface of the respective tooth 56 as the matrix material 18 is peeled away from the appliances 20. However, in instances where a relatively soft matrix material is employed or otherwise readily releases from the appliances 20, the use of a scaler to help avoid fracturing the fresh adhesive bond is optional.

Figure 5:
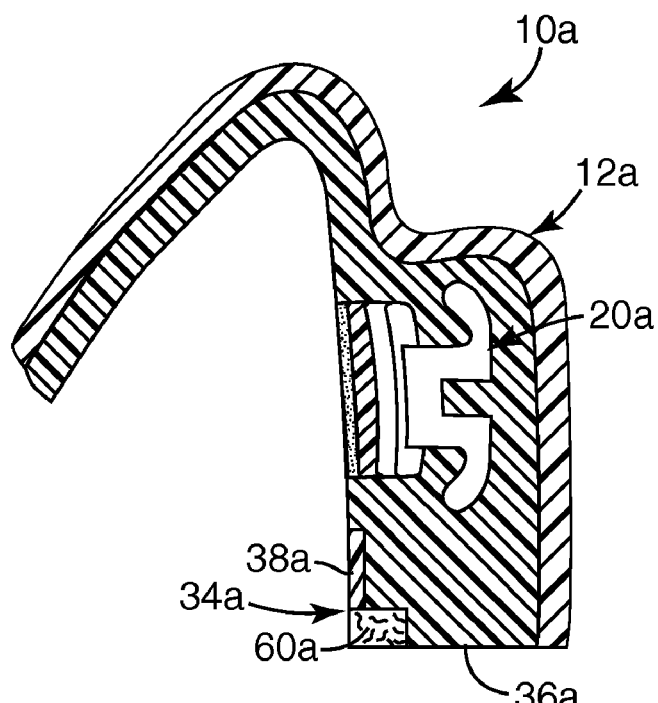
FIG. 5 is a view somewhat similar to FIG. 2 but showing an apparatus for indirect bonding according to another embodiment of the invention.

An apparatus 10a according to another embodiment of the invention is illustrated in FIG. 5. Except as set out in the paragraphs that follow, the apparatus 10a is substantially the same as the apparatus 10 described above and consequently a description of the similar aspects need not be repeated.

The apparatus 10a includes a moisture control structure 34a that extends between the path of the appliances and an outer edge 36a of a tray 12a. The moisture control structure 34a includes a film 38a which is substantially the same as the film 38. However, in this embodiment the passages of the film 38a are in communication with an absorbent material 60a that extends along the length of the outer edge 36a.

The absorbent material 60a may comprise any material suitable for absorbing oral fluids. Examples of suitable absorbent materials 36a include nonwoven materials, solid inorganic oxides that react with water to form the corresponding hydroxides, particularly those of elements in Groups 1-2 and 13-17 of the Periodic Table such as calcium oxide, zeolites that may or may not be in the form of finely divided powders, and cellulose (such as cotton). Preferably, the absorbent material 60a is encapsulated to facilitate retention of the absorbed fluids and covered with a section of film that is permeable to oral fluids.

As another option, the absorbent material 60a may comprise super-absorbent sodium polyacrylate granules that are optionally placed within an absorbent hydrophilic fiber fill. Preferably, the sodium polyacrylate granules and fiber fill are contained within a film that is preferably permeable to oral fluids. The sodium polyacrylate granules may be made in a manner similar to the manufacture of sodium polyacrylate granules that are used in disposable diapers.

As another alternative, the absorbent material 60a described in connection with the apparatus 10a may be placed within the plenum of the manifold 42 of the apparatus 10, which in turn, is connected by outlet tubing 50 to the source of vacuum 52. In this manner, the absorbent material 60a functions as a reservoir or holding chamber for the fluid that is subsequently drawn through the outlet tubing 50 upon application of sufficient vacuum pressure.

Figure 6:
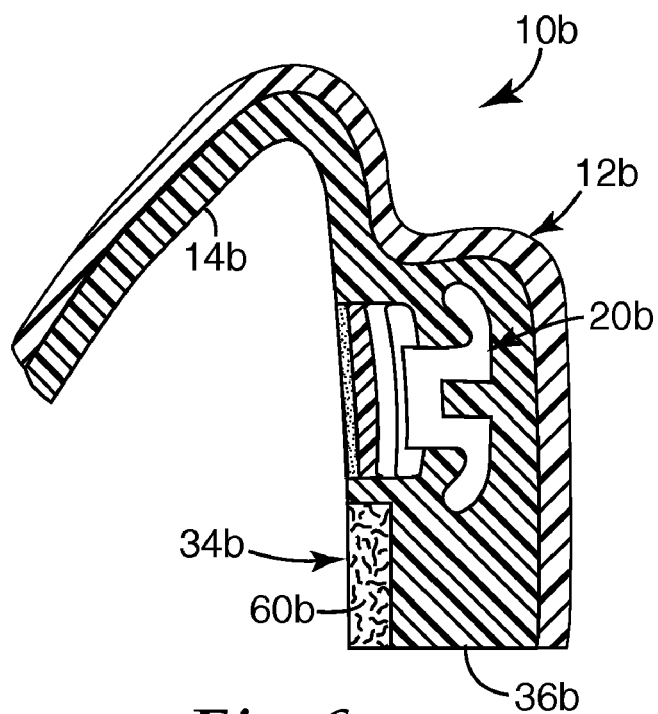
FIG. 6 is a view somewhat similar to FIG. 2 but showing an apparatus for indirect bonding according to yet another embodiment of the invention.

An apparatus 10b according to another embodiment of the invention is illustrated in FIG. 6. The apparatus 10b includes a tray 12b and a number of appliances 20b that are essentially the same as the tray 12 and appliances 20 respectively described above.

The apparatus 10b also includes an elongated moisture control structure 34b in the shape of a strip that extends along the area between the path of the appliances 20b and an outer edge 36b of the tray 12b. In this embodiment, the moisture control structure 34b comprises absorbent material 60b, but lacks a film with passages or similar structured structure with fluid flow channels. Instead, the absorbent material 60b is exposed along the channel 14b of the tray 12b for direct contact with the enamel surfaces of the patient's teeth.

The absorbent material 60b may comprise any of the absorbent materials 60a described above. Preferably, the absorbent material 60b comprises super-absorbent sodium polyacrylate granules that are placed within an absorbent hydrophilic fiber fill as described above in connection with the absorbent material 60a.

Optionally, the absorbent material 60b includes one or more layers of film that surround the sodium polyacrylate granules and absorbent fiber fill. For example, the sodium polyacrylate granules and fiber fill may be surrounded by an inner film layer made of a hydrophilic material that is permeable to moisture and has relatively small openings for the containment of fines. The inner layer may be surrounded by an outer film layer that is made of a moisture permeable hydrophobic material that feels dry to the touch, somewhat similar to the material used in disposable diapers.

Figure 7:
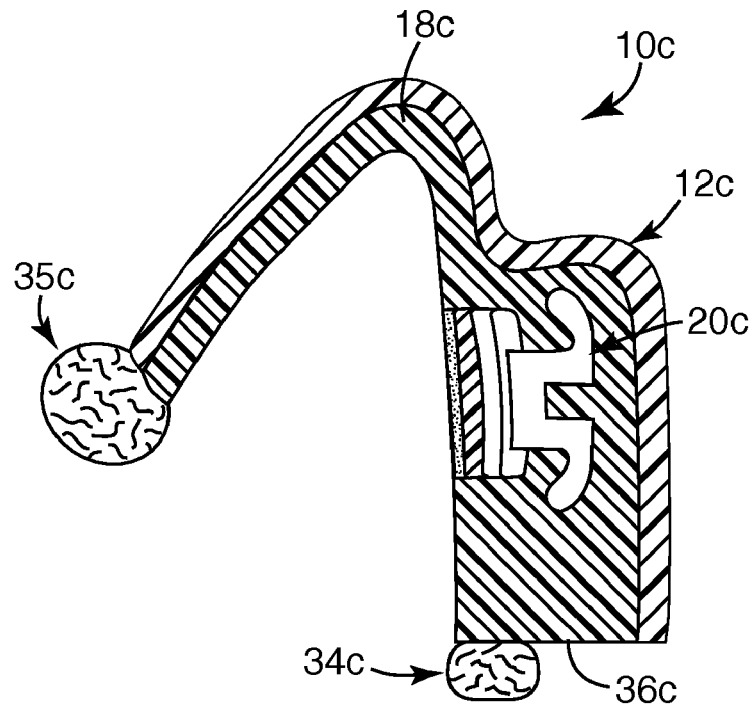
FIG. 7 is a view somewhat similar to FIG. 2 but showing an apparatus for indirect bonding according to still another embodiment of the invention.

An apparatus 10c for indirect bonding of orthodontic appliances according to another embodiment of the invention is illustrated in FIG. 7. The apparatus 10c includes a tray 12c and a number of appliances 20c detachably connected to the tray 12c. The apparatus 10c also includes a moisture control structure 34c that extends along a path located on a gingival side of an outer labial, gingival edge 36c of the tray 12c.

The moisture control structure 34c is similar to the moisture control structure 34b, in that it includes an absorbent material such as the absorbent materials 60a, 60b as described above.

The moisture control structure 34c includes an outer flexible film covering such as the "dry to the touch" moisture permeable hydrophobic film material mentioned above. This outer film covering is connected to matrix material 18c of the tray 12c by allowing the matrix material 18c to contact and penetrate the outer film covering prior to hardening of the matrix material 18c.

The moisture control structure 34c is pillow-like and readily deformable. As the apparatus 10c is placed over the patient's dental arch, the moisture control structure 34c can change in shape to conform to tooth structure or gingival tissue in areas adjacent the gingival margin. Optionally, the apparatus 10c may include moisture control structure 34b in addition to the moisture control structure 34c if desired. Other aspects of the apparatus 10c are essentially the same as described above in connection with the apparatus 10, 10a and 10b.

As an alternative to the moisture control structure 34c, or in addition to the moisture control structure 34c, the apparatus 10c includes a moisture control structure 35c as shown in FIG. 7. The moisture control structure 35c extends along the lingual side of the tray 12c and along an outer, lingual gingival edge of the tray 12c, and is particularly useful due to the relatively active nature of the salivary glands that reside under the tongue. As shown in the embodiment illustrated in FIG. 7, the moisture control structure 35c extends past the outer edge of the tray 12c in a direction away from the tray channel. In other aspects, the moisture control structure 35c is essentially the same as the moisture control structure 34c.

Figure 8:
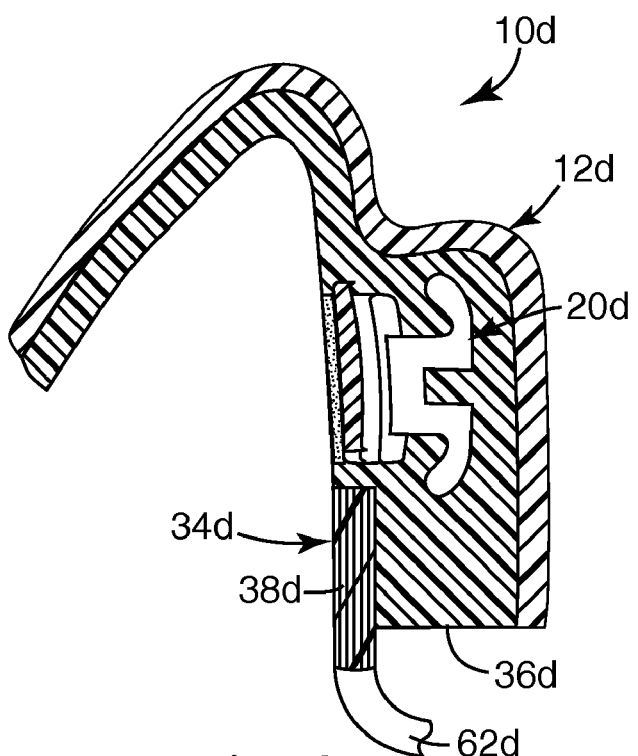
FIG. 8 is a view somewhat similar to FIG. 2 but showing an apparatus for indirect bonding according to an additional embodiment of the invention.

An apparatus 10d according to still another embodiment of the invention is illustrated in FIG. 8. The apparatus 10d includes a tray 12d and a number of appliances 20d received in the tray 12d. The apparatus 10d also includes a moisture control structure 34d for reducing the amount of moisture that might otherwise be present in areas adjacent the bonding base of the appliances 20d.

In this embodiment, the moisture control structure 34d comprises one or more stacks of film 38d, each of which has a microstructured surface with a plurality of flow channels or passages. Open ends of the passages are located adjacent the base of the appliances 20d. As one example, each film stack may be made by two to five layers of film. External to the tray 12d, the film stack is bound together by a length of tubing such as heat shrink tubing 62d.

Although not shown in the drawings, the end of the film stack remote from the appliances 20d may be connected to a quantity of absorbent material and/or a source of vacuum as described above. As one example, two film stacks are provided, each of which is located in one of the posterior regions of the tray 12d. As another alternative, a series of four, five or six film stacks are provided along the length of the tray 12d in spaced-apart relation. The film stacks may be connected together to a manifold that, in turn, is connected to absorbent material and/or a source of vacuum.

Except as described above, the apparatus 10d is essentially the same as the apparatus 10, 10a, 10b and 10c.

A number of other options and alternative constructions are also possible. For example, aspects of the moisture control structures 34b, 34c may be used in combination with the moisture control structure 34d of the apparatus 10d.

All of the patents and patent applications mentioned above are hereby incorporated by reference. The foregoing description is intended to exemplify various aspects of the invention and variations are possible. Consequently, the invention should not be deemed limited to the presently preferred embodiments described above, but instead only by a fair scope of the claims that follow and their equivalents.

The invention claimed is:

1. Apparatus for indirect bonding of orthodontic appliances comprising:
   a tray having a channel for receiving a patient's dental arch, the channel including an outer labial, gingival edge and an outer lingual, gingival edge;
   a number of orthodontic appliances detachably connected to the tray, the appliances being located in an occlusal direction from one of the outer edges and along a path in the channel; and
   an elongated, pliable moisture control structure extending along at least one of the outer edges and spaced from the appliances, wherein the moisture control structure is located in a gingival direction from the at least one of the outer edges, wherein the moisture control structure is configured to directly contact and conform to tooth surfaces as the dental arch is received in the channel to wipe away moisture from the tooth surfaces, and wherein the moisture control structure is configured to conform to gingival tissue in areas adjacent the gingival margin to substantially prevent additional moisture from entering the channel; wherein the moisture control structure comprises an absorbent material; wherein the moisture control structure also includes a flexible film extending over the absorbent material, said film comprising one or more layers and configured to contact tooth surfaces as the dental arch is received in the channel, and wherein said film is permeable to oral fluids.

2. Apparatus for indirect bonding of orthodontic appliances according to claim 1, wherein the tray comprises a hardened matrix material and wherein the matrix material is interconnected with at least one layer of the flexible film.

3. Apparatus for indirect bonding of orthodontic appliances according to claim 1 wherein the moisture control structure is capable of bulk movement along a labial-gingival axis relative to the tray.

4. Apparatus for indirect bonding of orthodontic appliances according to claim 1 wherein the moisture control structure extends past the outer edge in a direction away from the channel.

5. Apparatus for indirect bonding of orthodontic appliances according to claim 1 wherein the moisture control structure is located outside of the channel.

6. The apparatus of claim 1, wherein the moisture control structure has a deformable, pillow-like configuration.

7. The apparatus of claim 1, wherein the flexible film comprises a moisture permeable hydrophobic film material.

8. The apparatus of claim 1, wherein the flexible film comprises a inner film layer including hydrophilic material and an outer film layer including hydrophobic material.

9. The apparatus of claim 2, wherein the film remains interconnected with the matrix material during an indirect bonding procedure.

10. Apparatus for indirect bonding of orthodontic appliances comprising:
    a tray having a channel for receiving a patient's dental arch, the channel comprising a labial channel surface facing the labial surface of teeth when the tray is positioned on an upper or lower dental arch and a lingual channel surface facing the lingual surface of teeth when the tray is positioned on an upper or lower dental arch, wherein the labial channel surface and the lingual channel surface meet at a bottom of the channel, wherein the labial channel surface extends from the bottom of the channel to an outer labial, gingival edge, and wherein the lingual channel surface extends from the bottom of the channel to an outer lingual, gingival edge;

a number of orthodontic appliances detachably connected to the tray, the appliances being located within one of the labial channel surface and the lingual channel surface and along a path in the channel; and an elongated moisture control structure extending along at least one of the outer labial, gingival edge and the outer lingual, gingival edge, wherein the moisture control structure is located in a gingival direction from the at least one of the outer labial, gingival edge and the outer lingual, gingival edge; wherein the moisture control structure is configured to directly contact and conform to tooth surfaces as the dental arch is received in the channel to wipe away moisture from the tooth surfaces; and wherein the moisture control structure is configured to conform to gingival tissue in area adjacent the gingival margin; wherein the moisture control structure comprises an absorbent material; wherein the moisture control structure also includes a flexible film extending over the absorbent material, said film comprising one or more layers and configured to contact tooth surfaces as the dental arch is received in the channel, and wherein said film is permeable to oral fluids.

11. Apparatus for indirect bonding of orthodontic appliances according to claim 10, wherein the tray comprises a hardened matrix material interconnected with at least one of the flexible film layers.

12. Apparatus for indirect bonding of orthodontic appliances according to claim 10 wherein the moisture control structure is movable in bulk along a labial-gingival axis.

13. Apparatus for indirect bonding of orthodontic appliances according to claim 10 wherein the moisture control structure extends past the outer edge in a direction away from the channel.

14. Apparatus for indirect bonding of orthodontic appliances according to claim 10 wherein the moisture control structure is located outside of the channel.

15. The apparatus of claim 10, wherein the flexible film comprises a inner film layer including hydrophilic material and an outer film layer including hydrophobic material.

* * * * *

UNITED STATES PATENT AND TRADEMARK OFFICE
CERTIFICATE OF CORRECTION

PATENT NO.      : 8,021,146 B2                              Page 1 of 1
APPLICATION NO. : 11/422613
DATED           : September 20, 2011
INVENTOR(S)     : Cinader, Jr. et al.

It is certified that error appears in the above-identified patent and that said Letters Patent is hereby corrected as shown below:

<u>Column 3</u>
Line 8      Delete "DESCRIPTIONS" and insert -- DESCRIPTION --, therefor.

Signed and Sealed this
Fifteenth Day of May, 2012

David J. Kappos
*Director of the United States Patent and Trademark Office*